(12) United States Patent
Khaw et al.

(10) Patent No.: US 6,981,942 B2
(45) Date of Patent: Jan. 3, 2006

(54) TEMPORARY BLOOD CIRCULATION ASSIST DEVICE

(75) Inventors: Kenneth Khaw, Plainsboro, NJ (US); John K-J Li, Robbinsville, NJ (US)

(73) Assignee: University of Medicine and Dentristy of New Jersey, New Brunswick, NJ (US)

( * ) Notice: Subject to any disclaimer, the term of this patent is extended or adjusted under 35 U.S.C. 154(b) by 436 days.

(21) Appl. No.: 10/300,467

(22) Filed: Nov. 19, 2002

(65) Prior Publication Data
US 2003/0135086 A1 Jul. 17, 2003

Related U.S. Application Data

(60) Provisional application No. 60/331,909, filed on Nov. 19, 2001.

(51) Int. Cl.
*A61M 1/12* (2006.01)
(52) U.S. Cl. ............... 600/16; 623/3.1; 623/3.13
(58) Field of Classification Search ............ 600/16–18; 623/3.13–3.15; 128/899
See application file for complete search history.

(56) References Cited

U.S. PATENT DOCUMENTS

| | | | |
|---|---|---|---|
| 5,092,844 A | 3/1992 | Schwartz et al. | ............ 604/151 |
| 5,588,812 A | 12/1996 | Taylor et al. | ............... 417/356 |
| 5,749,855 A | 5/1998 | Reitan | ......................... 604/151 |
| 6,227,820 B1 | 5/2001 | Jarvik | .................... 417/423.12 |
| 6,245,007 B1 * | 6/2001 | Bedingham et al. | .......... 600/16 |

* cited by examiner

*Primary Examiner*—Robert E. Pezzuto
*Assistant Examiner*—Tammie Heller
(74) *Attorney, Agent, or Firm*—Licata & Tyrrell P.C.

(57) ABSTRACT

An inflatable circulation assist device is disclosed consisting of an inflatable stator housing an impeller with inflatable blades of varying shapes and sizes. The invention is introduced into the patient percutaneously. The circulation assist device is a small pump packaged into a compact form that is attached to a long flexible driveshaft. The pump is inserted along a guidewire to a target location, and then the pump is inflated. The circulation assist device's exterior is designed to expand only so much as to closely fit whatever cardiovascular system element in which it is placed for operation. The vascular assist device can be expanded either by inflation with a fluid. The driveshaft, which connects to the circulation assist device's impeller and extends outside the patient's body, is rotated by an external motor. After the circulation assist device is no longer needed, it is collapsed into a compact form and removed from the patient percutaneously.

46 Claims, 3 Drawing Sheets

TEMPORARY BLOOD CIRCULATION ASSIST DEVICE

CLAIM OF PRIORITY

This application claims priority to U.S. Provisional Application No. 60/331,909 filed on Nov. 19, 2001 which is incorporated as if fully set forth herein.

FIELD OF THE INVENTION

The present invention relates to the field of blood circulation assist devices.

BACKGROUND OF THE INVENTION

Certain medical conditions, traumas, and surgeries result in a patient's heart not being able to maintain adequate blood pressure to perfuse the patient's organ systems and tissues. Medical advances in circulation assist devices focus on this area wherein the heart or part of the heart is not able to contract and relax with the force necessary to maintain blood flow and pressure. These devices have been referred to ventricular assist devices, or "VAD." One specific type of VAD is a left ventricular assist device, or "LVAD."

In the simplest of terms, the right ventricle of the heart receives blood from the right atrium. The blood from the right atrium has come from the body and is thus deoxygenated. Once delivered from the right atrium to the right ventricle, the blood is pumped by the right ventricle through the three-leafed pulmonary valve and into the pulmonary artery. The blood has yet to be oxygenated in the lungs and so the pulmonary artery is the only artery that carries deoxygenated blood. After the blood has been oxygenated in the lungs, it is delivered to the left atrium. From the left atrium, the blood is pumped into the left ventricle where, in the healthy heart, it is pumped through the three-leafed aortic valve to the aorta to be distributed throughout the body. Circulation assist devices are most commonly indicated in left ventricular dysfunction, a dysfunction that does not allow the necessary perfusion of the body with oxygenated blood.

The intra-aortic balloon pump ("IABP") is the most commonly used LVAD to enhance a patient's cardiac output when the patient's heart fails to maintain a sufficient arterial blood pressure. An IABP, however, cannot create blood pressure when there is no left ventricle function, or during severe arrhythmia or fibrillation. U.S. Pat. No. 6,190,304 Downey discloses an IABP that is directed to creating additional blood pressure, but it does not indicate whether it can raise blood pressure from zero. Further, IABPs, in general, typically operate on a pulsate basis, and do not maintain constant blood pressure throughout the heart cycle. Moreover, IABPs typically use helium as the drive gas for the balloon and some require complex control systems. Vascular complications associated with IABPs can include perforation of the aortic wall, aortoiliac dissection, limb ischemic complications, etc.

Most LVAD surgically implanted pumps designed are as a "bridge to transplant" or "bridge to recovery." Because most of these pumps require surgical implantation, the patient must be a good surgical candidate. Many heart patients take thrombolytics or anti-coagulants and surgery is risky due to the potential for uncontrollable bleeding. In addition, these devices require considerable time to implant during a surgical procedure, and thus are not suitable for emergency situations, or situations where a patient is not in need of an assist device for any extended period.

Besides the IABPs, a number of other types surgical implanted LVAD pumps are currently available. Examples of these pumps include the Heartmate®, Thoratec®, Novacor® and Abiomed®. Axial flow LVAD pumps are available, but also require surgical implantation through the chest wall. Most of the axial flow pumps are in trial stages at this time, including the MicroMed DeBakey VAD® and the Jarvik 2000®.

A percutaneous axial flow pump was introduced in 1988 and commercially released in Germany in 1996. Called the Hemopump®, it consisted of an Archimedes screw driven by a cable within a cannula. An invention similar to the Hemopump is described in U.S. Pat. No. 5,092,844 (Schwartz et al), which describes a variety of pumping mechanisms in a sheath. Complications with the Hemopump may occur if the drive cable fractures or the cannula is expelled from the ventricle. The Hemopump was available in three variants, a 14 French version for percutaneous insertion, a 21 French version for introduction via graft anastomosis to the femoral artery and a 26 French version for direct insertion into the ascending aorta. The 21 French size Hemopump, however, could not always be successfully inserted through the femoral artery due to its size and a 14 French size Hemopump could only pump at rates up to 1.5 liters per minute.

Another percutaneous blood pump is described in U.S. Pat. No. 5,749,855 (Reitan), which uses an open propeller without a surrounding cylindrical pump housing. It requires a catheter with a lattice or bars to protect the aorta and the impeller. This device is being used only in the aorta and not in the left ventricle or the pulmonary artery.

There is current need for a blood circulation assist device that:
1. can increase cardiac output;
2. increase blood pressure when there is little or no ventricular function;
3. can maintain blood pressure throughout the heart cycle;
4. uses a simple drive and control system;
5. can be placed percutaneously via a guidewire in a very compact delivery package;
6. can be quickly placed and operated;
7. provides sufficient pumping capacity; and
8. does not traumatize the surrounding tissues.

SUMMARY OF THE INVENTION

Figure 1:
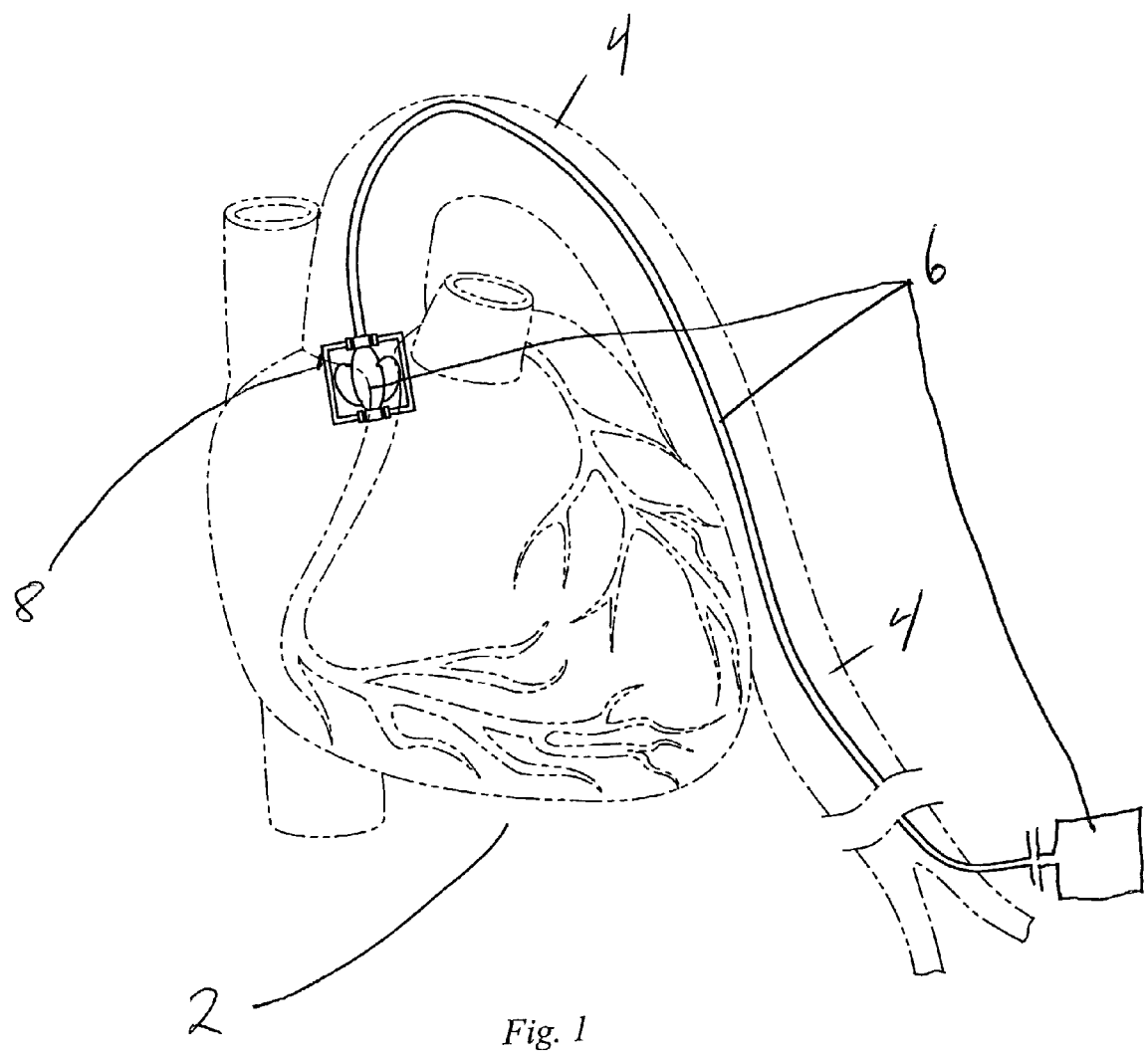
FIG. 1 depicts the location of the blood assist device in the aortic valve.

The present invention intends to provide an axial flow blood circulation assist device that can be delivered as a compact package through a 10 French (or smaller) arterial or venous sheath(s) under fluoroscopy or transthoracic echocardiogram, and then expanded when positioned in the desired operational location. The present invention may be designed as a temporary device in emergent and surgical situations where time is of the essence. One preferred embodiment may be a circulation assist device that may be expandable by inflation and may be positioned across the aortic and/or pulmonic valve, which could support blood pressure continuously through the heart cycle. This circulation assist device has benefits over the other PVADs in that the circulation assist device of over other ventricular assist devices may include an enclosed impeller section, which could prevent laceration, perforation and possible collapse of the left ventricle chamber.

Unlike an IABP, the circulation assist device may unload the ventricular chamber completely, allowing the ventricular chamber to rest so that the ventricular chamber does not have to carry the load of pumping to maintain blood flow. In most cases however, the circulation assist device does not need to unload the ventricular chamber completely, it just has to assist in maintaining the systemic blood pressure.

After a left side circulation assist device is placed and has begun operating, a physician may use his or her clinical judgment to assess whether the assisted flow is enough to maintain adequate blood pressure. If the left chamber is completely unloaded and the blood pressure is still low from emptying of left atrium, another inflatable circulation assist device may be expanded in the right side of the heart to increase the blood flow to the lungs, and thus to the left ventricle. An increase in blood flow to the left side of the heart may allow more flow to the systemic side (arterial side) and may allow the blood pressure to rise to an acceptable level. A parameter to determine the number of PVADs is the blood pressure on the systemic side.

Two circulation assist devices, one on either side of the heart, may be needed if the left ventricle is non-functional, such as in end-stage dilated cardiomyopathy or in cardiogenic shock from extensive myocardial infarction. In such a case, the circulation assist device on the left side operates to maintain the blood pressure and may need additional blood flow from an circulation assist device on the right side to prevent the partial or total collapse of the left side of the heart caused by venturi or suction effects at high flow rates.

In other applications, such as open-heart surgery, two circulation assist devices may be needed. If the surgeon wants to minimize the movement of the left side of the heart during a procedure such as a coronary artery bypass graft ("CABG"), then it is desirable to minimize the left ventricular volume. To maintain a minimal left ventricular volume, while maintaining adequate flow and blood pressure, left and right side circulation assist devices may be needed.

If the present invention is used on both sides of the heart, complete heart function may be maintained even if the heart has stopped. Indications for usage includes but should not be limited to cardiogenic shock (during acute myocardial infarction, with or without thrombolytics), intractable ventricular tachycardia and/or fibrillation. Once the circulation assist device is placed, percutaneous coronary intervention (such as angioplasty, stent, thrombectomy, artherectomy) and open heart CABG may be performed if warranted. The circulation assist device may also be used as a bridge to a more permanent left ventricular assist device.

A preferred embodiment of the circulation assist device may replace a majority of IABPs used in cardiogenic shock patients. The PVAD may also be used to bridge to permanent left ventricular assist devices in patients affected with severe left ventricular failure or cardiomyopathy who may not be able to undertake emergent or urgent open-heart surgery. The PVAD may decrease some complications associated with IABPs, such as leg ischemia, aortic plaque rupture, atherosclerotic embolization or renal failure. The PVAD may also be used across the pulmonic valve to maintain pulmonary flow. By using two PVADs, one across the aortic valve and one across the pulmonic valve, the physician may easily assist the heart in pumping blood in both the left and right heart chambers.

The invention may require fluoroscopy and/or echocardiogram to accurately place it in the left ventricular outflow tract, or other blood vessel or valve. In some applications, such as when placed across the aortic valve, an accurate placement may be important to proper operation of the circulation assist device.

Potential applications for use of the circulation assist device may include patients with: (1) cardiogenic shock; (2) intractable ventricular arrhythmia such as ventricular fibrillation or ventricular tachycardia; (3) during ventricular tachycardia ablation procedure where there is hemodynamic instability; (4) during supraventricular tachycardia ablation procedure, where there is hemodynamic instability; and (5) right ventricular failure causing hemodynamic instability.

Other uses for the blood circulation assist device may also be indicated, such as improving circulation to other parts of the body, the brain during or after a stroke for example. Of course, different applications may require the assist device to be positioned at a location appropriate to the application. All that is needed is an entry blood vessel or valve sufficiently large enough to accept the sheathed device prior to expansion including the stator housing and impeller adapted to fit the particular blood vessel or valve after expansion.

This invention is contemplated for short-term usage of 3 to 7 days; before the patient undergoes a definite procedure or terminates the use of the circulation assist device. In addition, the patient may need an echocardiogram to measure aortic root diameter so an appropriate sized device may be used. In cases where the assist device is used on other parts of the body besides the aorta, similar measurement techniques may be needed to determine the appropriate sized assist device.

DETAILED DESCRIPTION OF THE INVENTION

The references cited in this disclosure are incorporated by reference as if fully set forth herein. FIG. 1 depicts a diagrammatic representation of the heart 2 in a frontal view. The aorta 4 is shown with the circulation assist device 6 across the aortic valve 8.

Figure 2:
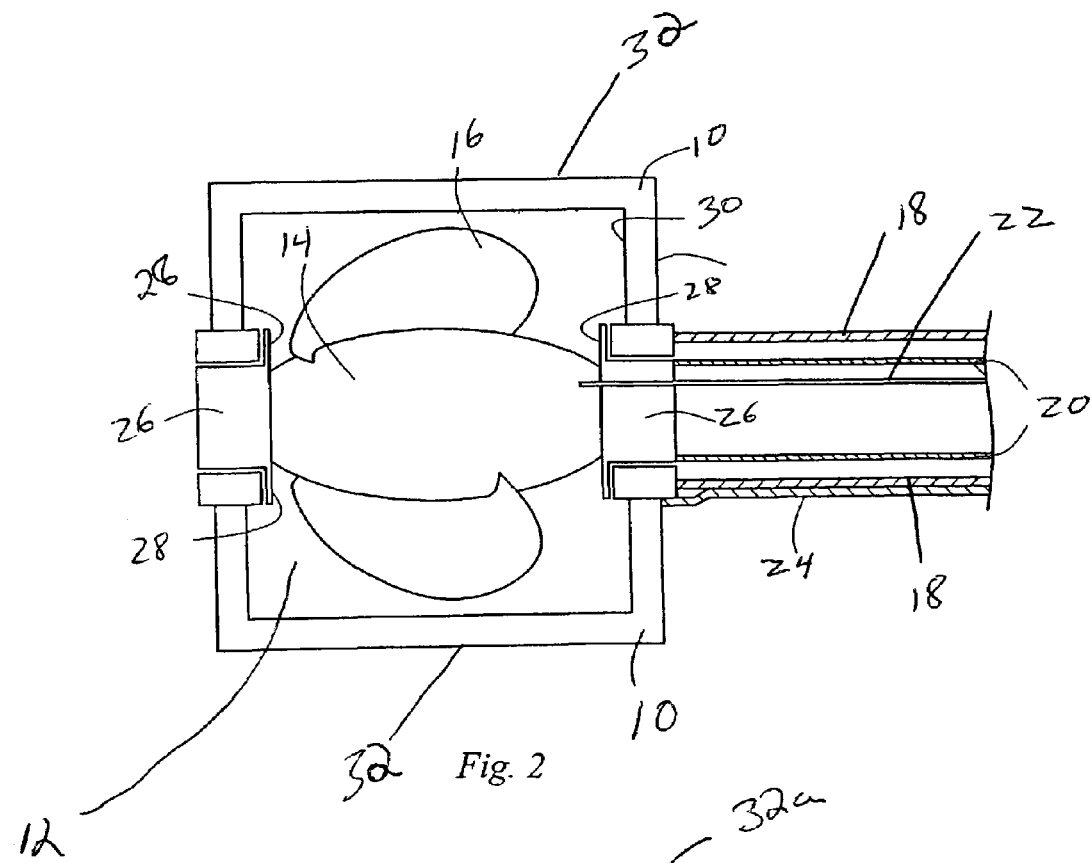
FIG. 2 is a frontal section of the outer sheath, driveshaft, and impeller inflation tube.

FIG. 2 depicts a transverse plane view of the distal portion of one embodiment of the circulation assist device 6. The inflated stator housing 10 and impeller 12 are shown. The impeller 12 comprises the impeller body 14 and the impeller blades 16. In this depicted embodiment, the blades are ear-shaped and situated on an oval impeller body 14. In an alternative embodiment, depicted in FIG. 7, the blades 16 are semi-circular-shaped. It is contemplated that different blade shapes may be used to effect different goals for the invention and that those blades will be associated appropriate shafts for the blades. The number of blades on the impeller is similarly variable.

Also depicted in FIG. 2 is an outer sheath 18 that surrounds a first drive shaft 20 and an impeller inflation tube 22. Located longitudinally along the length of the outer sheath 18 is the stator housing inflation tube 24. At each end of the impeller body 14 are impeller shafts 26, the proximal one of which is connected to first drive shaft 20. Collars 28 may be connected with the impeller shafts 26 to keep the impeller 12 in the proper position within the stator housing 10. During operation, the outer sheath 18 which surrounds a first drive shaft may remain stationary while the first drive shaft 20 and impeller 12 rotate.

The impeller 12 rotates within the interior surface of the stator housing 30. The stator housing exterior surface 32 is contemplated to contact the chosen vascular structure, the aortic valve 6 depicted in FIG. 1, for example.

Figure 3:
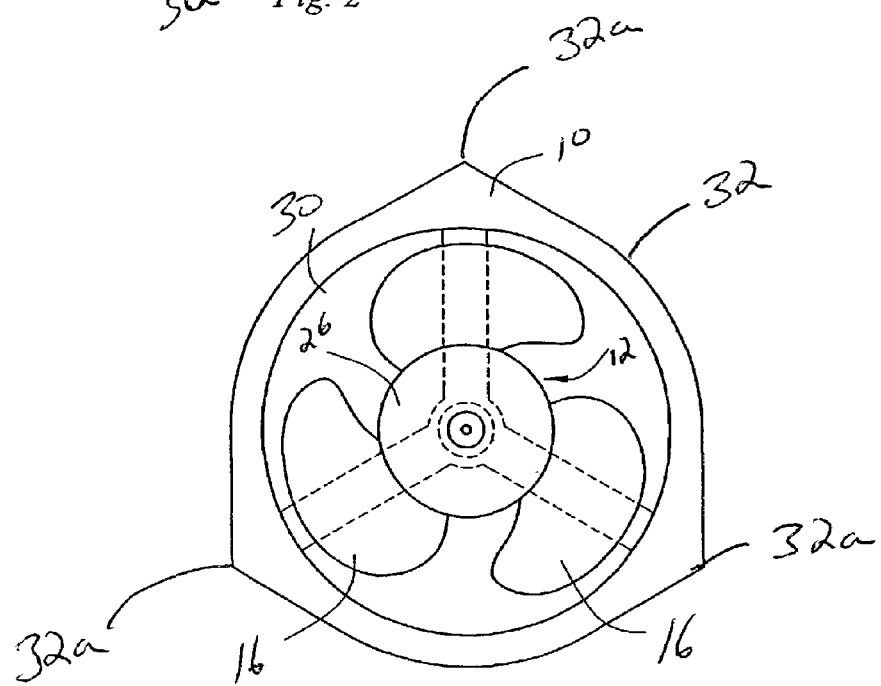
FIG. 3 is an end view of the expanded stator housing and impeller.

FIG. 3 is a transverse plane section of the distal end of the circulation assist device. At the stator housing exterior surface are number of corners 32a that may be created as the stator housing 10 is inflated across a particular valve, a tri-cuspid valve, for example, which would create three corners 32a.

Figure 4:
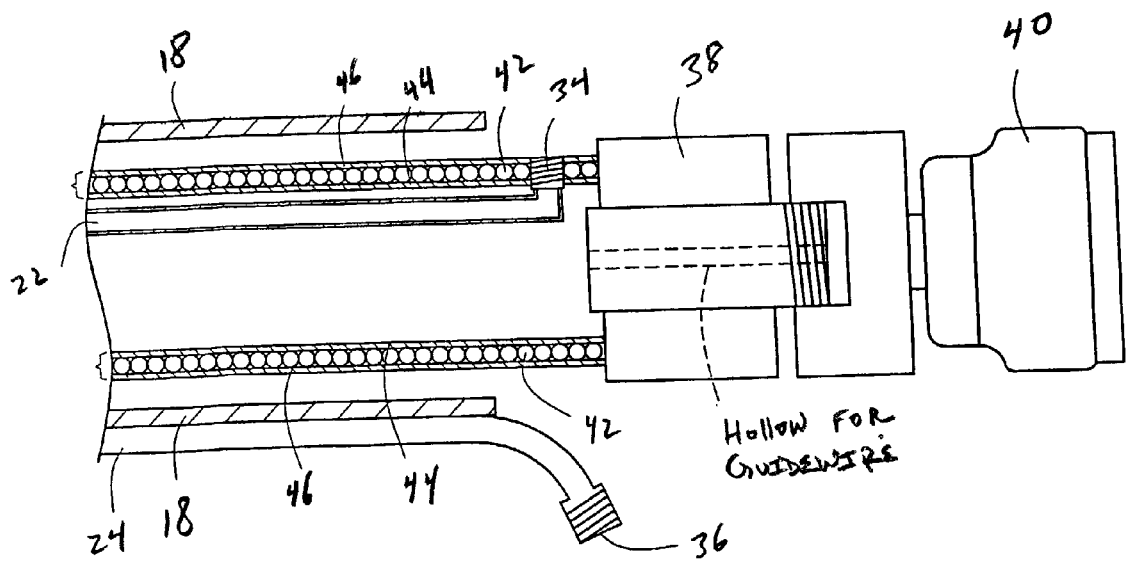
FIG. 4 is a lateral view depicting the impeller and collets and frame for the stator housing.

FIG. 4 depicts a sagital section of the outer sheath 20, the first drive shaft 20, the impeller inflation tube 22 and the stator housing inflation tube 24. The impeller inflation tube 22 contains an impeller inflation port 34 at its proximal end and the stator house inflation tube 24 contains a stator house inflation port 36 at its proximal end. The first drive shaft 20 is connected to a second driveshaft 38 in either a permanent or removable manner, and the second drive shaft 38 may be removably connected to the motor 40. FIG. 4 further depicts one embodiment of the first drive shaft 20 in which the first drive shaft 24 is constructed a metal coil 42 within an inner drive shaft sheath 44 and an outer drive shaft sheath 46.

Figure 5:
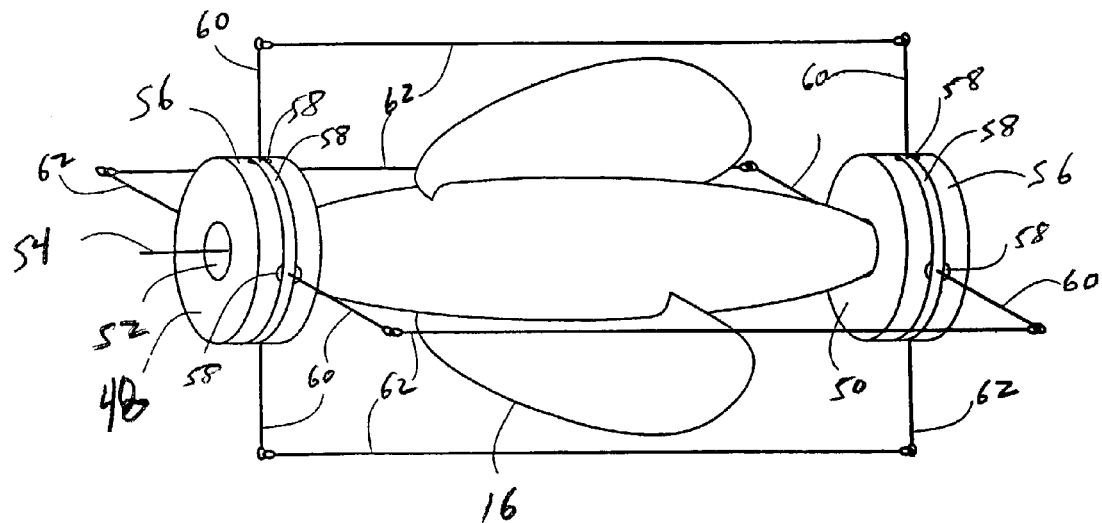
FIG. 5 is a transverse section of the outer sheath, driveshaft, inflation tubes and ports, solid shaft, and motor.

Referring to FIG. 5, one embodiment of the support system for the impeller 12 and the stator housing may be appreciated. The stator housing 10 (which has been removed in this figure) may have a first collet 48 and a second collet 50 at either end that serves to support the impeller shaft 26 and may provide structure for the stator housing 10. The collets 48, 50 have a hollow center 52 that is oriented along impeller axis 54. The collets 48, 50 may have a sufficient outer wall 56 dimension to hold a retainer ring 58 made of surgical steel or another suitable, surgical grade substance. The collets may be constructed of any suitable material including metal, PTFE, Delrin, nylon, etc. The, outer sheath 18 may be attached the collets 48, 50 and the outer sheath 18 could be molded as an integral unit. In the collet outer wall 56, indentations 60 may be used to provide attachment points for spokes 60 attached to the retainer ring 58, which spokes may, extend radially from the collet's outer wall 38 like spokes extending from a hub and creating spokes 60. The spokes 60 may act as reinforcements for the stator housing 10, At the end of the spokes 60, that end away from the retainer ring 58 an outer wire 62 connects the spokes 60 of one collet 48 to the corresponding spoke of the other collet 50, and this outer wire may be substantially parallel to the impeller axis 64.

Each outer wire 62, then, is a common outer wire 62 between two corresponding spokes 60. Outer wires 62 may either be molded into the stator housing 10, attached to or molded within either the stator housing interior surface 30 or stator surface exterior surface. The outer wires 62 may also be laminated to the interior or exterior surface of the stator housing, 30, 32. In this manner, collets 48, 50 spokes 60, and outer wires 62 may form a frame for the stator housing 10, providing the stator housing 10 with reinforcement.

The spokes 60 and outer wires, 48 may be constructed of any surgical grade, rigid material such as stainless steel or inert plastics. The spoke and wire connection 64 may be a hinge means wherein a hinge is created at the spoke and wire connection 64. The hinge means may be a simple tubular plastic covering around the outer end of the spoke and at both ends of the common outer wire that connects to the spokes. The spokes and outer wire ends may be friction fit into the tubular plastic covering or the covering may extend over the length of both the spokes and outer wire. In another embodiment, a continues tubular plastic covering may extend from where a spoke meets a first collet and continue to also hold the common outer wire. The tubular covering would freely bend and fold in such a manner that they may simply fold down as the stator housing is deflated and collapsed to be packaged for use or removed from the patient. Folding may be accomplished by simply moving the framework created by the spokes and the outer wires in either direction along the impeller axis. Alternatively, the spokes and outer wires may be made of metal with sufficient memory properties to revert to its prepackaged shape when the stator housing is inflated. Various numbers of spokes and outer wires with different attachment points and different types of connections may be used.

It is contemplated that the circular assist device will be able to fit over a guidewire and thus, except for the motor, has a hollow center.

The outer sheath 18 and first drive shaft sheath 44, 46 may be constructed from or coated with low-friction materials, such as PTFE (polytetrafluoroethylene (Teflon®), FEP (fluorinated ethylene propylene copolymer), Rulon® (TFE fluorocarbon), acetal (Delrin), the near-frictionless carbon coating from Argonne Laboratories, or other suitable material.

The impeller 12 may be constructed of a plastic, such as PET or any other material that can be inflated but substantially maintains its preformed shape. In other words, it is not overly expandable when fully inflated. The material should be capable of expansion by inflation, but after it reaches a certain pressure, the expansion should be minimal, despite variations in pressure, to prevent the impeller 12 from becoming oversized or significantly distorted. In a preferred embodiment, both the impeller body 14 and the impeller blades 16 may be inflated. An impeller inflation tube 22 inflates the impeller 12. The impeller inflation tube 22 may be routed from outside of the patient's body near the motor 40 and through the first drive shaft 20 and may terminate at the impeller inflation port 34 wherein there may be a one-way valve similar to a tire valve near the terminus of the first drive shaft 20. The impeller 12, first drive shaft 20, and impeller inflation tube 22 may rotate as a single unit. Although one preferred embodiment may have a single impeller, additional impellers may be used in a single stator housing 10 or multiple stator housings.

The impeller 12 may be hollow through its central portion (not shown), to accommodate a guidewire. The hollow center may also extend through both impeller shafts 20, 38 to provide a continuous route along a guidewire from the second drive shaft 38, through the central hollow of the first driveshaft 20 and on to the motor 40. The proximal end of circulation assist device may be equipped with a very tight-fitting seal (not shown), which closes after the guidewire is retracted. This tight-fitting seal may leak slightly, but blood intrusion may be minimized by filling the first drive shaft 20 with saline, possibly. Alternatively, to minimize blood leakage, a hemostasis valve may be used at or near the distal end second driveshaft 32. Numerous hemostasis valves are commercially available. The hemostasis valve may be used alone, or in conjunction with the tight-fitting seal, and/or the saline.

The stator housing 10 may be constructed of a plastic material that is expandable via inflation. Again, the stator housing 10 is inflated via the stator housing inflation tube 30. The inflation tubes for the impeller and stator housing may be constructed of any suitable flexible material that resists expansion, and the impeller housing inflation tube 26 may be constructed of a flexible material that is durable enough to withstand constant rotation within the outer sheath 18 during the operational life of the circulation assist device.

Alternatively, to achieve a wider range of fit, the stator housing exterior surface 32 may be sufficiently pliable upon inflation to expand to fit within a range of cardiovascular elements without the need for large numbers of specialized shapes and sizes. The stator housing exterior surface 32 may be made of a softer durometer than the stator housing interior surface 30, such that exterior surface 32 would gently expand upon inflation while interior surface 30 remains rigid by comparison. Alternatively, the interior surface 30 and exterior surface 32 may be made of the same material, but exterior surface 32 could be thinner and therefore subject to more expansion than interior surface 30.

In an alternative embodiment, spokes 60 and outer wires 62 may be constructed of one piece of material. In such an embodiment, the construction material may preferably be a material that has appropriate memory characteristics to expand out to its original shape, and yet provides enough rigidity to support the stator housing.

In another embodiment, the impeller 12 may be supported by two bearings at either end of the impeller 12 between impeller 12 and collets 48, 50. The bearings may be mechanical bearings, such as ball or needle bearings, or plain bearings made of metal, PTFE, nylon, or other suitable material. In the case of a plain bearing, the collets 48, 50 may be entirely constructed of the bearing material, eliminating the need for a separate bearing in the collets 48, 50. Numerous other bearings that have been used in blood pumps may also be suitable, including the ball and cup bearing described in U.S. Pat. No. 5,588,812 (Taylor et al.), or magnetic bearings such as those described in U.S. Pat. No. 6,227,820 (Jarvik). To keep the impeller from contacting collets, 48, 50, the impeller shaft 26 may be equipped with collars 28 that may be attached to each end of impeller 12 and inserted into collet 48, 50. The impeller shaft 26 and the collars 28 may be one piece, and may be constructed of a durable low friction plastic. Although, like the collet using a plain bearing they may be constructed of bearing material.

The impeller 12 may be inflated with liquid such as sterile saline or another biologically compatible liquid. The stator housing 10 may be similarly inflated. Other biologically compatible liquids may also be used, including liquids that provide contrast during fluoroscopy. The liquid may be of sufficient mass and/or pressure so the impeller 12 will not distort during rotation. In an alternative embodiment, the impeller blades may be made of rigid or semi-rigid materials, which are solid and do not require inflation.

The impeller 12, fusiform shaped and the impeller body 14 may have a modified fusiform shape that tapers on both ends to reduce drag and shear forces on the blood. The impeller blades 16 may extend radially from the impeller body 22 towards the housing stator 2. This design is consistent with the contemplated temporary nature of the described circulation assist device.

A seal may be positioned between the first drive shaft 20 and the outer sheath 18 to prevent blood intrusion. The outer sheath 18 may be filled with saline under a pressure that is slightly higher than the patient's blood pressure to prevent blood from entering. Other biologically compatible liquids may be used.

In one preferred embodiment, the circulation assist device may be introduced through the femoral artery or vein as an axial flow pump pre-wrapped in a delivery sheath as a small packaged unit. The physician may first introduce a guidewire into the femoral artery and route it to the target position. The circulation assist device, in an unexpanded small packaged unit, may then be threaded onto the guidewire outside the patient's body, introduced into the femoral artery and routed along the guidewire. When the small packaged unit reaches the target location, the physician may remove the guidewire. At the target location, the delivery sheath would be retracted, and both the stator housing 10 and impeller 12 would be inflated. Where the circulation assist device is used across a heart valve, the circulation assist device's stator housing 10 and impeller 12 would be positioned across the aortic or pulmonic valve.

The stator housing 10 may be adapted to fit the particular cardiovascular element in which the assist device will operate. Typical cardiovascular elements may include heart valves, either pulmonic or aortic, and blood vessels of sufficient size. Various sizes and shapes of stator housings may be needed for various sized cardiovascular elements, depending on the individual patient. It is contemplated that the circulation assist device may be available in sizes that reasonably relate to the anatomy of the cardiovascular system. With respect to valves in the heart, it should be remembered that the valves might tend to close around the stator housing. Thus, the practitioner using the vascular assist device should limit the chosen size of the stator housing and impeller. Proper placement and fit may beneficially lead to an effective seal.

The circulation assist device may be sheathed and delivered over a 0.025-inch or 0.035-inch guidewire. The size of the impeller 12 and stator housing 10 is variable depending on the anatomy of the patient and the area of the anatomy selected for circular assistance. It is contemplated that the circulation assist device at its distal portion will range in size between 0.5 cm to 5.0 cm. It is contemplated that sizes of the circular assist device at its distal portion may be more commonly used at 2.0 to 3.0 cm. In an embodiment where the stator housing exterior surface 32 is shaped to fit a valve with a particular shape, such as the three-leafed aortic or pulmonic valve, the circulation assist device may be rotated to properly seat across the valve. The orientation of the circulation assist device may be ascertained prior to or during inflation by sonographic or other suitable means. To ascertain proper orientation, the circulation assist device may be constructed with an element that provides a visual cue as to the circulation assist device's orientation, such as a strip of material that is sonographically or fluoroscopically or radiographically distinct. The circulation assist device may then be rotated by rotating the outer sheath 18, which is outside the patient's body to properly orient the stator housing's exterior surface 32 to the valve's shape.

Upon the proper placement, the circulation assist device is inflated using liquid or air. Liquid is the preferred method of inflation due to the many known complications of air pressure devices in the art. Once inflated, the impeller 12 may be rotated via a first drive shaft 20 that extends outside the patient's body. The first drive shaft 20 and impeller 12 may be rotated by an external electric motor 40 to move blood in and out of the left ventricle into the aorta and to assist and/or to maintain blood pressure. The rotation speed of the impeller 12 is determined by factoring the pitch, number and size of the chosen impeller blades 16. For example, for a circulation assist device with two blades pitched at between 15–20 degrees, the rotation of the impeller is selected at least about 700 to 2000 RPM. If desired, the rotation of the motor 8 may be pulsed to cause pulsate flow.

The first drive shaft 20 and extends through a percutaneous opening. The outer sheath 18 may remain stationary while the first drive shaft 20 rotates within the outer sheath 18. The materials for the outer sheath 18 and first drive shaft sheath, 44, 46 may be sufficiently durable during the expected life cycle of the assist device. The second drive shaft 38 is contemplated to have a durometer greater than the first drive shaft 20. Thus, the first drive shaft 20 will be more flexible than the second drive shaft 38.

EXAMPLE I

Aortic Valve Placement

A patient suffers the effects of left ventricular dysfunction and a procedure using the described invention may be chosen. The patient may be prepared for the procedure in the customary manner. The femoral artery approach may be chosen and the circulation assist device may be advanced to the aortic valve. The described circulation assist device may be then placed across the aortic valve to provide blood to the body due to the left ventricular dysfunction. The stator housing may be positioned across the aortic valve after the stator housing exterior has been adapted to fit that particular patient's aortic valve, with the valve size determined by ultrasound measurement or other suitable means. Here, the stator housing may be adapted to sit across the aortic valve in which the anulus fibrosus may measure greater than 3 cm. A two blade semi-lunar impeller may be chosen. The pitch of the blades may be between 15 and 20 degrees. The stator housing may be positioned to hold the valve open while the valve closes against the stator housing. A RPM may be selected at 2000 RPM and the impeller may then move blood across the aortic valve. A one-way valve in the circulation assist device may be used to prevent regurgitation of blood in the event that the pump is stopped for any reason.

A flow rate of 3–4 L/min may be measured in the aorta just proximal to the circulation assist device.

EXAMPLE II

Pulmonic Valve Placement

Due to right ventricular dysfunction, it may be desirable to use the invention across the pulmonic valve. The procedure may be performed as above. Here, the direction of impeller rotation may be used to draw blood either into our out of the right ventricle. Blood may be pulled from the heart towards the proximal aspect of the circulation assist device and moved across the pulmonary valve. The metal coil in the first drive shaft may be rotated in the reverse direction, and impeller 12 may be adapted to operate in the reverse direction. Alternatively the impeller may be rotated in the same direction as in the aortic valve embodiment with impeller blades reversed and adapted to move blood in the opposite direction. A one-way valve may also be employed. In this case, it may be desirable to select a tow-blade impeller with a classic tear drop shape. A pitch of 15–20 degrees may be selected and the RPM chosen at between 700–2000 RPM. A flow rate of 1.8 L/min may be measured in the pulmonary vein.

It is to be understood, that even though numerous characteristics and advantages of the invention have been set forth in the foregoing description and examples, together with the detail of the structure and function of the invention, the disclosure is illustrative only and changes may be made in detail, especially in manners of shape, size, and arrangement of the parts within the principles of the invention to the full extent indicated by the broad general meaning of the terms in which the appended claims are expressed.

What is claimed is:

1. A circulation assist device comprising:
   at least one inflatable impeller having an impeller shaft and at least two blades;
   a first collet and a second collet supporting the impeller shaft;
   an inflatable stator housing connected to the first collet and the second collet and having an interior and an exterior surface enclosing the impeller;
   a first drive shaft connected to a second drive shaft connected to the impeller;
   an outer sheath surrounding at least a portion of the first drive shaft and connected to the stator housing; and
   a motor connected to the first drive shaft.

2. The circulation assist device of claim 1 wherein the impeller and blades are inflated with a liquid.

3. The circulation assist device of claim 2 wherein the liquid is a biologically compatible liquid.

4. The circulation assist device of claim 1 wherein the impeller and blades are inflated with a gas.

5. The circulation assist device of claim 4 wherein the gas is a biologically compatible gas.

6. The circulation assist device of claim 1 wherein the stator housing is inflated with a liquid.

7. The circulation assist device of claim 6 wherein the liquid is a biologically compatible liquid.

8. The circulation assist device of claim 1 wherein the stator housing is inflated with a gas.

9. The circulation assist device of claim 8 wherein the gas is a biologically compatible gas.

10. The circulation assist device of claim 1 further comprising a stator housing inflation port located proximal to the terminus of the outer sheath.

11. The circulation assist device of claim 1, further comprising an impeller inflation port located proximal to the terminus of the first drive shaft.

12. The circulation assist device of claim 1, wherein the stator housing has an interior surface supported by a frame connected to the first collet and the second collet.

13. The circulation assist device of claim 12 wherein the frame comprises at least two spokes connected to the second collet.

14. The circulation assist device of claim 12 wherein the frame further comprises at least two spokes connected to the second collet.

15. The circulation assist device of claim 12 further comprising a number of outer wires which connect to at least one spoke on the first collet and to at least one spoke on the second collet.

16. The circulation assist device of claim 15 wherein the at least one spoke connected to the first collet is connected to the outer wire by a hinge and the at least one spoke connected to the second collet is connected to the outer wire by a hinge means.

17. The circulation assist device of claim 16 wherein the at least one spoke connected to the first collet and the at least one spoke connected to the second collet are each connected to a common outer wire wherein the common outer wire is substantially parallel to the axis of the impeller.

18. The circulation assist device of claim 1, wherein the first drive shaft and the second drive shaft are hollow.

19. The circulation assist device of claim 9 wherein the first drive shaft is of lesser durometer than the second drive shaft.

20. The circulation assist device of claim 1 wherein the impeller is connected with an inflation tube that extends through the hollow of the first drive shaft and terminates at an inflation port located proximal to the motor.

21. The circulation assist device of claim 12 wherein the frame can be folded by moving the outer wires and the stator housing along the axis of the impeller.

22. The circulation assist device of claim 1 wherein the impeller blades have a particular shape.

23. The circulation assist device of claim 22 wherein the particular shape of the impeller blades may be selected from the group consisting of semi-circular, teardrop, ear, kidney, racquet and serpentine shaped blades.

24. A percutaneous circulation assist device comprising:
at least one inflatable impeller having an impeller shaft and at least two blades;
a first collet and a second collet supporting the impeller shaft;
an inflatable stator housing connected to the first collet and the second collet and having an interior and an exterior surface enclosing the impeller;
a first drive shaft connected to a second drive shaft connected to the impeller;
an outer sheath surrounding at least a portion of the first drive shaft and connected to the stator housing; and
a motor connected to the first drive shaft.

25. The percutaneous circulation assist device of claim 24 wherein the impeller and blades are inflated with a liquid.

26. The percutaneous circulation assist device of claim 25 wherein the liquid is a biologically compatible liquid.

27. The percutaneous circulation assist device of claim 24 wherein the impeller and blades are inflated with a gas.

28. The percutaneous circulation assist device of claim 27 wherein the gas is a biologically compatible gas.

29. The percutaneous blood circulation assist device of claim 24 wherein the stator housing is by inflated with a liquid.

30. The percutaneous circulation assist device of claim 29 wherein the liquid is a biologically compatible liquid.

31. The percutaneous assist device of claim 24 wherein the stator housing is inflated with a gas.

32. The percutaneous circulation assist device of claim 31 wherein the gas is a biologically compatible gas.

33. The percutaneous circulation assist device claim of 24 further comprising a stator housing inflation port located proximal to the terminus of the outer sheath.

34. The percutaneous circulation assist device of claim 24 further comprising an impeller inflation port located proximal to the terminus of the first drive shaft.

35. The percutaneous circulation assist device of claim 24 wherein the stator housing has an interior surface supported by a frame connected to the first collet and the second collet.

36. The percutaneous circulation device of claim 35 wherein the frame comprises at least two spokes connected to the first collet.

37. The percutaneous circulation assist device of claim 35 wherein the frame comprises at least two spokes connected to the second collet.

38. The percutaneous circulation assist device of claim 35 further comprising a number of outer wires which connect to at least one spoke on the first collet and to at least one spoke on the second collet.

39. The percutaneous circulation assist device of claim 35 wherein the at least one spoke connected to the first collet is connected to the outer wire by a hinge and the at least one spoke connected to the second collet is connected to the outer wire by a hinge means.

40. The percutaneous circulation assist device of claim 39 wherein the at least one spoke connected to the first collet and the at least one spoke connected to the second collet are each is connected to a common outer wire wherein the common outer wire is substantially parallel to the axis of the impeller.

41. The percutaneous circulation assist device of claim 24 wherein the first drive shaft and the second drive shaft are centrally hollow.

42. The percutaneous circulation assist device of claim 24 wherein the first drive shaft is of lesser durometer than the second drive shaft.

43. The percutaneous circulation assist device of claim 24 wherein the impeller is connected with an inflation tube that extends through the interior of the first drive shaft and terminates at an inflation port located proximal to the motor.

44. The percutaneous circulation assist device of claim 35 wherein the frame can be folded by moving the outer wires and the stator housing along the axis of the impeller.

45. The percutaneous circulation assist device of claim 24 wherein the impeller blades have a particular shape.

46. The percutaneous circulation assist device of claim 24 wherein the particular shape of the impeller blades may be selected from the group consisting of semi-circular, teardrop, ear, kidney, racquet and serpentine shaped blades.

* * * * *